US009789318B2

(12) United States Patent
An et al.

(10) Patent No.: US 9,789,318 B2
(45) Date of Patent: *Oct. 17, 2017

(54) METHOD AND APPARATUS FOR OPTIMIZING MULTI-SITE PACING USING HEART SOUNDS

(71) Applicant: Cardiac Pacemakers, Inc., St. Paul, MN (US)

(72) Inventors: Qi An, Blaine, MN (US); Pramodsingh Hirasingh Thakur, Woodbury, MN (US); Yinghong Yu, Shoreview, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/882,849

(22) Filed: Oct. 14, 2015

(65) Prior Publication Data
US 2016/0106986 A1    Apr. 21, 2016

Related U.S. Application Data

(60) Provisional application No. 62/065,474, filed on Oct. 17, 2014.

(51) Int. Cl.
*A61N 1/36* (2006.01)
*A61N 1/365* (2006.01)
(Continued)

(52) U.S. Cl.
CPC ......... *A61N 1/36585* (2013.01); *A61N 1/056* (2013.01); *A61N 1/3627* (2013.01);
(Continued)

(58) Field of Classification Search
CPC .. A61N 1/3686; A61N 1/0563; A61N 1/3622; A61N 1/36578; A61N 1/36585
See application file for complete search history.

(56) References Cited

U.S. PATENT DOCUMENTS 6,477,406 B1    11/2002   Turcott
7,209,786 B2    4/2007    Brockway et al.
(Continued)

FOREIGN PATENT DOCUMENTS

WO    WO-2016061176 A1    4/2016
WO    WO-2016061202 A1    4/2016

OTHER PUBLICATIONS

"St. Jude Medical ReceivesCE MarkApproval of MultiPoint Pacing CRT-D", http://investors.sjm.com/investors/financial-news/news-release-details/2013/St-Jude-Medi al-Receives-CE-Mark-Approval-of-MulliPoint-Pacing-CRT-D/default.aspx (Received from the web: Oct. 14, 2015), (Jun. 24, 2013), 1-2.
(Continued)

*Primary Examiner* — Paula J Stice
(74) *Attorney, Agent, or Firm* — Schwegman Lundberg & Woessner, P.A.

(57) ABSTRACT

An example of a system for pacing through multiple electrodes in a ventricle includes a sensing circuit to sense cardiac signal(s), a pacing output circuit to deliver pacing pulses, a heart sound sensor to sense a heart sound signal, and a control circuit to control the delivery of the pacing pulses. The control circuit includes a heart sound detector to detect heart sounds using the heart sound signal, an electrical event detector to detect cardiac electrical events using the cardiac signal(s), a measurement module to measure an optimization parameter using the detected heart sounds, and an optimization module to approximately optimize one or more pacing parameters using the measured optimization parameter. The one or more pacing parameters include an electrode configuration parameter specifying one or more electrodes selected from the multiple electrodes in the ventricle for delivering ventricular pacing pulses to that ventricle.

20 Claims, 8 Drawing Sheets

(51) Int. Cl.
*A61N 1/05* (2006.01)
*A61N 1/362* (2006.01)
*A61N 1/368* (2006.01)

(52) U.S. Cl.
CPC ......... *A61N 1/3684* (2013.01); *A61N 1/3686* (2013.01); *A61N 1/36578* (2013.01)

(56) References Cited

U.S. PATENT DOCUMENTS

| | | | |
|---|---|---|---|
| 7,431,699 B2 | 10/2008 | Siejko et al. | |
| 8,160,700 B1 | 4/2012 | Ryu et al. | |
| 8,583,230 B2 | 11/2013 | Ryu et al. | |
| 8,617,082 B2 | 12/2013 | Zhang et al. | |
| 9,272,148 B2 | 3/2016 | Ghosh | |
| 2004/0172079 A1 | 9/2004 | Chinchoy | |
| 2005/0102002 A1 | 5/2005 | Salo et al. | |
| 2005/0137631 A1 | 6/2005 | Yu et al. | |
| 2008/0004667 A1 | 1/2008 | Arcot-krishnamurthy et al. | |
| 2008/0177191 A1* | 7/2008 | Patangay ............. | A61B 5/0402 600/509 |
| 2009/0054945 A1 | 2/2009 | Patangay et al. | |
| 2009/0254139 A1 | 10/2009 | Bjorling | |
| 2011/0098700 A1 | 4/2011 | Tamai et al. | |
| 2012/0165892 A1 | 6/2012 | Min | |
| 2012/0253419 A1 | 10/2012 | Rosenberg et al. | |
| 2012/0296228 A1* | 11/2012 | Zhang ................. | A61B 5/0006 600/513 |
| 2012/0296387 A1 | 11/2012 | Zhang et al. | |
| 2013/0030484 A1 | 1/2013 | Zhang et al. | |
| 2013/0053716 A1 | 2/2013 | Zhang et al. | |
| 2013/0178786 A1* | 7/2013 | Wariar ............... | A61N 1/36564 604/20 |
| 2013/0204312 A1 | 8/2013 | Gill et al. | |
| 2013/0289640 A1 | 10/2013 | Zhang et al. | |
| 2016/0106983 A1 | 4/2016 | An et al. | |

OTHER PUBLICATIONS

Pappone, Carlo, et al., "Cardiac Resynchronization Therapy with Multisite Left Ventricular Pacing ImprovesAcute Hemodynamic Response in Patients", Abstract 13412; 2012 AHA, (2012), 1-2.
"U.S. Appl. No. 14/882,923, Non Final Office Action mailed Nov. 10, 2016", 11 pgs.
"International Application Serial No. PCT/US2015/055446, International Search Report mailed Dec. 22, 2015", 5 pgs.
"International Application Serial No. PCT/US2015/055446, Written Opinion mailed Dec. 22, 2015" , 6 pgs.
"International Application Serial No. PCT/US2015/055497, International Search Report mailed Jan. 11, 2016", 5 pgs.
"International Application Serial No. PCT/US2015/055497, Written Opinion mailed Jan. 11, 2016", 5 pgs.
"St. Jude Medical Receives CE Mark Approval of MultiPoint Pacing CRT-D", http://investors.sjm.com/investors/financial-news/news-release-details/2013/St-Jude-Medical-Receives-CE-Mark-Approval-of-MultiPoint-Pacing-CRT-D/default.aspx (Received from the web: Oct. 14, 2015), (Jun. 24, 2013), 1-2.
Pappone, Carlo, et al., "Cardiac Resynchronization Therapy with Multisite Left Ventricular Pacing Improves Acute Hemodynamic Response in Patients", Abstract 13412; 2012 AHA, (2012), 1-2.

* cited by examiner

METHOD AND APPARATUS FOR OPTIMIZING MULTI-SITE PACING USING HEART SOUNDS

CLAIM OF PRIORITY

This application claims the benefit of priority under 35 U.S.C. §119(e) of U.S. Provisional Patent Application Ser. No. 62/065,474, filed on Oct. 17, 2014, which is herein incorporated by reference in its entirety.

CROSS-REFERENCE TO RELATED APPLICATIONS

This application is related to commonly assigned U.S. Provisional Patent Application Ser. No. 62/065,479, entitled "METHOD AND APPARATUS FOR AMBULATORY OPTIMIZATION OF MULTI-SITE PACING USING HEART SOUNDS," filed on Oct. 17, 2014, assigned to Cardiac Pacemakers, Inc., which is hereby incorporated by reference in its entirety.

TECHNICAL FIELD

This document relates generally to cardiac rhythm management and more particularly to method and apparatus for delivering pacing pulses to multiple sites in at least one of the ventricles in a heart and optimization of a pacing configuration.

BACKGROUND

The heart is the center of a person's circulatory system. It includes an electro-mechanical system performing two major pumping functions. The left side of the heart, including the left atrium (LA) and the left ventricle (LV), draws oxygenated blood from the lungs and pumps it to the organs of the body to supply their metabolic needs for oxygen. The right side of the heart, including the right atrium (RA) and the right ventricle (RV), draws deoxygenated blood from the body organs and pumps it to the lungs where the blood gets oxygenated. These pumping functions result from contractions of the myocardium (cardiac muscles). In a normal heart, the sinoatrial (SA) node, the heart's natural pacemaker, generates electrical impulses, called action potentials, that prop agate through an electrical conduction system to various regions of the heart and excite the myocardial tissues of these regions. Coordinated delays in the propagations of the action potentials in a normal electrical conduction system cause the various portions of the heart to contract in synchrony and result in efficient pumping function.

A blocked or otherwise damaged electrical conduction system causes irregular contractions of the myocardium, a condition generally known as arrhythmia. Arrhythmia reduces the heart's pumping efficiency and hence diminishes the blood flow to the body. A deteriorated myocardium has decreased contractility, also resulting in diminished blood flow. A heart failure patient usually suffers from both a damaged electrical conduction system and a deteriorated myocardium. Cardiac pacing therapy has been applied to treat arrhythmia and heart failure. For example, cardiac resynchronization therapy (CRT) app lies left ventricular or biventricular pacing to restore synchronized contractions. A CRT system may include electrodes placed in the RA, the RV, and the LV to deliver pacing pulses to one or more of these heart chambers for restoring cardiac synchrony by artificially coordinating atrioventricular and/or interventricular myocardial activation delays.

SUMMARY

An example (e.g., "Example 1") of a system for delivering pacing pulses through a plurality of electrodes to a heart is provided. The heart has first and second ventricles. The plurality of electrodes includes a plurality of first ventricular electrodes placed in or on the first ventricle. The system includes a cardiac sensing circuit, a pacing output circuit, a heart sound sensor, and a control circuit. The cardiac sensing circuit is configured to sense one or more cardiac signals. The pacing output circuit is configured to deliver the pacing pulses. The heart sound sensor is configured to sense a heart sound signal. The control circuit is configured to control the delivery of the pacing pulses using cardiac electrical events and a plurality of pacing parameters. The control circuit includes a heart sound detector, an electrical event detector, a measurement module, and an optimization module. The heart sound detector is configured to detect heart sounds using the heart sound signal. The electrical event detector is configured to detect the cardiac electrical events using at least one cardiac signal of the sensed one or more cardiac signals. The measurement module configured to measure at least one optimization parameter indicative of hemodynamic response to the delivery of the pacing pulses using the detected heart sounds. The optimization module is configured to approximately optimize one or more pacing parameters of the plurality pacing parameters using the measured at least one optimization parameter. The one or more pacing parameters include an electrode configuration parameter specifying one or more first ventricular electrodes selected from the plurality of first ventricular electrodes for delivering first ventricular pacing pulses of the pacing pulses to the first ventricle.

In Example 2, the subject matter of Example 1 may optionally be configured such that the one or more pacing parameters further include one or more pacing timing parameters specifying timing of delivery of the first ventricular pacing pulses for each of the specified one or more first ventricular electrodes.

In Example 3, the subject matter of Example 2 may optionally be configured such that the one or more pacing timing parameters include one or more atrio-ventricular delays.

In Example 4, the subject matter of Example 2 may optionally be configured such that the one or more pacing timing parameters include one or more intra-ventricular delays.

In Example 5, the subject matter of Example 2 may optionally be configured such that the one or more pacing timing parameters include one or more inter-ventricular delays.

In Example 6, the subject matter of any one or any combination of Examples 1-5 may optionally be configured such that the heart sound detector is configured to detect first heart sounds (S1) using the heart sound signal, the measurement module is configured to measure an S1 amplitude using the detected S1, and the optimization module is configured to approximately optimize the one or more pacing parameters for maximizing the S1 amplitude.

In Example 7, the subject matter of any one or any combination of Examples 1-6 may optionally be configured such that the heart sound detector is configured to detect third heart sounds (S3) using the heart sound signal, the measurement module is configured to measure an S3 amplitude using the detected S3, and the optimization module is configured to approximately optimize the one or more pacing parameters for minimizing the S3 amplitude.

In Example 8, the subject matter of any one or any combination of Examples 1-7 may optionally be configured such that the electrical event detector is configured to detect Q-waves or R-waves using the at least one cardiac signal, the wherein the heart sound detector is configured to detect first heart sounds (S1) using the heart sound signal, the measurement module is configured to measure an pre-ejection period (PEP) as a time interval between a Q-wave or R-wave and a subsequently adjacent occurrence of the S1, and the optimization module is configured to approximately optimize the one or more pacing parameters for minimizing the PEP.

In Example 9, the subject matter of any one or any combination of Examples 1-8 may optionally be configured such that the heart sound detector is configured to detect first heart sounds (S1) and second heart sounds (S2) using the heart sound signal, the measurement module is configured to measure an ejection time (ET) as a time interval between an occurrence of the S1 and a subsequently adjacent occurrence of the S2, and the optimization module is configured to approximately optimize the one or more pacing parameters for maximizing the ET.

In Example 10, the subject matter of any one or any combination of Examples 1-7 may optionally be configured such that the electrical event detector is configured to detect Q-waves or R-waves using the at least one cardiac signal, the wherein the heart sound detector is configured to detect first heart sounds (S1) and second heart sounds (S2) using the heart sound signal, the measurement module is configured to measure an pre-ejection period (PEP) as a time interval between a Q-wave or R-wave and a subsequently adjacent occurrence of the S1 and measure an ejection time (ET) as a time interval between an occurrence of the S1 and a subsequently adjacent occurrence of the S2, and the optimization module is configured to approximately optimize the one or more pacing parameters for minimizing a ratio of the PEP to the ET.

In Example 11, the subject matter of any one or any combination of Examples 1-10 may optionally be configured such that the electrical event detector is configured to detect R-waves using the at least one cardiac signal, the wherein the heart sound detector is configured to detect second heart sounds (S2) using the heart sound signal, the measurement module is configured to measure an R-S2 interval between an R-wave and a subsequently adjacent occurrence of the S2, and the optimization module is configured to approximately optimize the one or more pacing parameters for minimizing the R-S2 interval.

In Example 12, the subject matter of any one or any combination of Examples 1-11 may optionally be configured to include an implantable medical device and a first implantable ventricular lead. The implantable medical device includes at least the cardiac sensing circuit, the pacing output circuit, and the control circuit. The first implantable ventricular lead is configured to be coupled to the implantable medical device and including the plurality of first ventricular electrodes.

In Example 13, the subject matter of Example 12 may optionally be configured such that the first implantable ventricular lead is an implantable left ventricular lead.

In Example 14, the subject matter of Example 12 may optionally be configured such that the first implantable ventricular lead is an implantable right ventricular lead.

In Example 15, the subject matter of any one or any combination of Examples 12-14 may optionally be configured to further include an atrial lead and a second ventricular lead. The atrial lead is configured to be coupled to the implantable medical device and including one or more atrial electrodes. The second ventricular lead configured to be coup led to the implantable medical device and including one or more second ventricular electrodes.

An example of a method (e.g., "Example 16") for pacing a heart having first and second ventricles is also provided. The method includes delivering pacing pulses to the heart through at least a plurality of first ventricular electrodes placed in or on the first ventricle, sensing one or more cardiac signals indicative of cardiac electrical events, sensing a heart sound signal indicative of heart sounds, measuring at least one optimization parameter indicative of hemodynamic response to the delivery of the pacing pulses using at least the heart sound signal, approximately optimizing one or more pacing parameters of a plurality of pacing parameters using the measured at least one optimization parameter, and controlling the delivery of the pacing pulses using the cardiac electrical events and the plurality of pacing parameters. The one or more pacing parameters includes an electrode configuration parameter specifying one or more first ventricular electrodes selected from the plurality of first ventricular electrodes for delivering first ventricular pacing pulses of the pacing pulses to the first ventricle.

In Example 17, the subject matter of the one or more pacing parameters as found in Example 16 may optionally further include one or more pacing timing parameters specifying timing of delivery of the first ventricular pacing pulses for each of the specified one or more first ventricular electrodes.

In Example 18, the subject matter of any one or any combination of Examples 16 and 17 may optionally include measuring a first heart sound (S1) amplitude using the hearing sound signal and approximately optimizing the one or more pacing parameters for maximizing the S1 amplitude.

In Example 19, the subject matter of any one or any combination of Examples 16-18 may optionally include measuring a third heart sound (S3) amplitude using the hearing sound signal and approximately optimizing the one or more pacing parameters for minimizing the S3 amplitude.

In Example 20, the subject matter of any one or any combination of Examples 16-19 may optionally include measuring a pre-ejection period (PEP) using the one or more cardiac signals and the hearing sound signal and approximately optimizing the one or more pacing parameters for minimizing the PEP.

In Example 21, the subject matter of any one or any combination of Examples 16-20 may optionally include measuring an ejection time (ET) using the hearing sound signal and approximately optimizing the one or more pacing parameters for maximizing the ET.

In Example 22, the subject matter of any one or any combination of Examples 16-19 may optionally include measuring a pre-ejection period (PEP) using the one or more cardiac signals and the hearing sound signal, measuring an ejection time (ET) using the hearing sound signal, and approximately optimizing the one or more pacing parameters for minimizing a ratio of the PEP to the ET.

In Example 23, the subject matter of any one or any combination of Examples 16-22 may optionally include measuring an R-S2 interval between a ventricular depolarization (R-wave) and a subsequently adjacent occurrence of sound heart sound (S2) using the one or more cardiac signals and the hearing sound signal, and approximately optimizing the one or more pacing parameters for minimizing the R-S2 interval.

This Summary is an overview of some of the teachings of the present application and not intended to be an exclusive or exhaustive treatment of the present subject matter. Further details about the present subject matter are found in the detailed description and app ended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
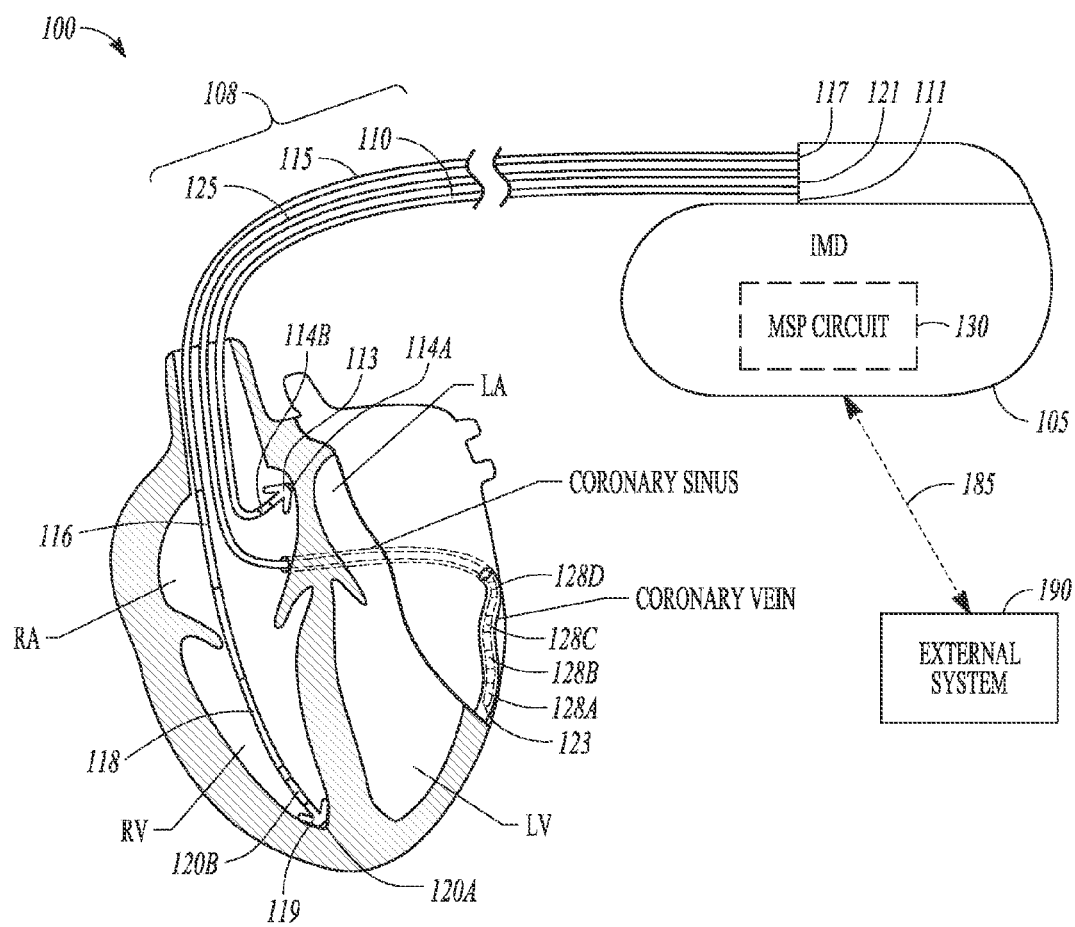
FIG. 1 is an illustration of an embodiment of a cardiac rhythm management (CRM) system and portions of an environment in which the CRM system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

It should be noted that references to "an", "one", or "various" embodiments in this disclosure are not necessarily to the same embodiment, and such references contemplate more than one embodiment.

This document discusses a method and system for multi-site pacing ("MSP") that includes optimization of the pacing parameters using heart sounds. The system is configured to deliver pacing pulses to a patient's heart. The patient's heart includes the right atrium (RA), the right ventricle (RV), the left atrium (LA), and the left ventricles. In this document, "multi-site pacing", or "MSP", includes delivering pacing pulses to a plurality of pacing sites in the patient's heart with the delivery to each site of the plurality of pacing sites individually controllable, and the plurality of pacing sites includes at least two pacing sites in the LV, at least two pacing sites in the RV, or at least two pacing sites in each of the LV and RV. "Single-site pacing" includes delivering pacing pulses to one or more pacing sites in the patient's heart with the delivery to each site of the one or more pacing sites individually controllable, and the one or more pacing sites include one pacing sites in the LV, one pacing site in the RV, or one pacing site in each of the LV and RV of the patient's heart. A pacing electrode is placed at each pacing site of the plurality of pacing sites. The delivery to each site of the plurality of pacing sites is individually controllable as, for example, the at least two sites in one ventricular can be paced at different times (e.g., with an inter-site or inter-electrode delay) during each cardiac cycle. An "MSP system" includes a pacing system that can be programmed for MSP or single-site pacing.

Cardiac resynchronization therapy ("CRT") has been applied to treat heart failure patient. An implantable CRT system may include, for example, an implantable biventricular pacing device that delivers pacing pulses to a pacing site in each of the RV and the LV through a lead including an electrode placed at the pacing site. It has been learned that effectiveness of such biventricular pacing therapy in treating heart failure in a patient may depend on the locations of the pacing sites, i.e., where the electrodes are placed in the RV and the LV. The optimal locations may change as the condition of the patient's heart changes. After the implantation of the leads with the electrodes placed at the pacing sites, however, the locations of the pacing sites cannot be adjusted. It has also been learned that a single pacing site in a ventricle, even when optimally located, may not produce the desirable pattern of activation of that ventricle.

The present system can include an implantable MSP device that can be programmed to deliver pacing pulses to multiple pacing sites in at least one of the ventricles of the patient's heart, using at least one implantable lead including multiple electrodes each placed on one pacing site of the multiple pacing sites. When being configured to treat heart failure patients by restoring synchrony in cardiac contractions, the MSP may be referred to as multi-site CRT. In various embodiments, the probability of delivering pacing pulses to an efficient pacing site in a ventricle can be increased by increasing the number of pacing sites in that ventricle. The efficient pacing site is the pacing site (electrode location) that allows the delivery of the pacing pulses to produce the intended effect. In various embodiments, faster and more physiologic activation of a ventricle can be achieved by delivering pacing pulses to more pacing sites (electrode locations) in the ventricle. After implantable of the implantable MSP device and the implantable lead, the multiple electrodes allow for selection of one or more pacing sites in the ventricle where the multiple electrodes are placed. In various embodiments, the efficacy of the MSP delivered from such a system depends on, among other things, the selection of pacing sites in the heart and the relative timing of pacing in those pacing sites (inter-site or inter-electrode pacing delays). Thus, optimization of the MSP may include optimizing the selection of the pacing sites and the timing of pacing in each selected pacing site. For the ventricle in which the multiple electrodes are placed, the optimization can identify an approximately optimal electrode set, which can include one or more electrodes (each corresponding to a pacing site), and determine timing of delivering the pacing pulses to each electrode of the identified approximately optimal electrode set. In various embodiments, the optimization can include comparison among various electrodes in single-site pacing, various electrodes in MSP, and various multi-site activation delay options.

In various embodiments, the performance of the MSP can be evaluated and optimized using heart sounds. Heart sounds include the "first heart sound" or S1, the "second heart sound" or S2, the "third heart sound" or S3, the "fourth heart sound" or S4, and their various sub-components. S1 is known to be indicative of, among other things, mitral valve closure, tricuspid valve closure, and aortic valve opening. S2 is known to be indicative of, among other things, aortic valve closure and pulmonary valve closure. S3 is known to be a ventricular diastolic filling sound often indicative of certain pathological conditions including heart failure. S4 is known to be a ventricular diastolic filling sound resulted from atrial contraction and is usually indicative of pathological conditions. The term "heart sound" hereinafter refers to any heart sound (e.g., S1) and any components thereof (e.g., M1 component of S1, indicative of Mitral valve closure). In this document, "heart sound" includes audible and inaudible mechanical vibrations caused by cardiac activity that can be sensed with an accelerometer or microphone. Accordingly, the scope of "acoustic energy" in this document extends to energies associated with such mechanical vibrations. Unless noted otherwise, S1, S2, S3, and S4 refer to the first, second, third, and fourth heart sounds, respectively, as a heart sound type, or as one or more occurrences of the corresponding type heart sounds, depending on the context.

In this document, "user" includes a physician or other caregiver who examines and/or treats a patient using one or more of the methods and apparatuses reported in the present document.

To treat heart failure, various parameters indicative of status of heart failure in a patient, such as one or more parameters indicative of the patient's hemodynamic response to cardiac pacing, are measured using at least heart sounds. In some embodiments, various parameters indicative of status of heart failure in the patient are measured using both heart sounds and cardiac electrical events. Examples of parameters indicative of the patient's hemodynamic response to cardiac pacing include systolic time intervals (STIs) that may be measured between cardiac electrical and/or mechanical events related to systole and diastolic time intervals (DTIs) that may be measured between cardiac electrical and/or mechanical events related to diastole. For example, as heart failure worsens, pre-ejection period ("PEP") increases and ejection time ("ET") decreases. STIs and DTIs can be determined using pressure waveforms, but can also be estimated using heart sound waveforms. The time interval between the Q or R-wave and the subsequently adjacent S1 can be an estimate of the PEP. The time interval between the S1 and the subsequently adjacent S2 can be an estimate of the ET. Certain Heart sound amplitudes are also correlated to the worsening of heart failure. For example, diminishing of S1 amplitude may be indicative of weakening of heart contractility (which can be measured by the rate of LV pressure change, LV dP/dt), and S3 may be caused by elevation of filling pressure and/or stiffer ventricular wall, which are known to be associated with heart failure.

In various embodiments, the present system detects heart sounds and optimizes MSP by adjusting one or more pacing parameters for one or more of the following: (1) maximizing S1 amplitude, (2) minimizing S3 amplitude, (3) minimizing paced PEP interval, (4) maximizing ET, (5) minimizing the ratio of PEP to ET, and (6) minimizing R-S2 interval (the time interval between the R-wave and the subsequent occurrence of S2. In various embodiments, the present system detects diastolic interval (time interval between the S2 to the subsequently adjacent R-wave) and verifies that the detected diastolic interval is within an acceptable range as a safety check. The adjustment of the one or more pacing parameters is limited by keeping the diastolic interval within the acceptable range.

In various embodiments, MSP can be optimized during and/or after implantation of the implantable MSP device and leads. In this document, optimization of MSP includes optimization of one or more pacing parameters in an MSP system that can be configured to MSP or single-site pacing. The optimization of MSP may determine whether MSP or single-site pacing should be applied, pacing sites, and timing parameters associated with each of the pacing sites. Thus, the optimization of MSP may result in the optimal pacing configuration being a single-site pacing configuration.

Because the patient's heart failure status and/or other conditions may change after the implantation, an implantable system cap able of MSP may be prescribed even if single-site pacing is determined to be the optimal configuration at the time of the implantation. In various embodiments, the present system performs re-optimization of pacing parameters according to a predetermined schedule or as a need is indicated after the implantation of the implantable MSP device and leads.

In various embodiments, the present system adjusts the pacing parameters using ambulatory optimization of MSP. The ambulatory optimization allows pacing parameters in an MSP system to be adjusted to approximately maximize benefit to the patient chronically. In various embodiments, an acute optimization of MSP is performed during, or upon completion of, the implantation of the implantable system, and ambulatory optimization of MSP is performed thereafter. In one embodiment, the acute optimization and the ambulatory optimization (re-optimization) use the same optimization procedure, such as when the optimization procedure is performed using the implantable system. In another embodiment, the acute optimization and the ambulatory optimization (re-optimization) use different optimization procedures, such as when the optimization procedure is performed using external sensor(s) and/or other devices what may not be readily available during a re-optimization.

In one embodiment, a re-optimization of MSP is trigged using a timer programmed with a predetermined schedule, such as on a periodic basis.

In another embodiment, a re-optimization of MSP is triggered by a detection of a specified-type event. The specified-type event may be indicative of a change in the status of heart failure in the patient. In one embodiment, an event that is indicative of worsening of the heart failure is specified as an event that triggers the re-optimization of MSP. In another embodiment, an event that is indicative of either worsening or improvement of a conduction associated with the patient's heart failure may be specified as an event that triggers the re-optimization of MSP if a change in the conduction suggests that the current pacing parameters may no longer be approximately optimal. In various embodiments, the present system may include one or more specified-type events each triggering the re-optimization of MSP. Examples of the one or more specified-type events detected using heart sounds include (1) a substantial decrease in S1 amplitude, (2) a substantial change in S1 waveform morphology, (3) a substantial increase in S3 amplitude, (4) a substantial change in a systolic time interval, and (5) a substantial change in a diastolic time interval. Other examples of the one or more specified-type events include (1) a substantial increase in an impedance phase loop area, (2) a substantial decrease in the maximum rate of change in impedance (maximum dZ/dt), and (3) a substantial increase in QLV sensed as an interval between a global peak (e.g., a Q-wave on a surface electrocardiogram or unipolar ventricular electrogram) and a local peak (an LV electrogram sensed at the pacing site). In various embodiments, the specified-type events may include any one or more events that can be indicative of a need for the re-optimization of MSP.

In various embodiments, the one or more pacing parameters to be adjusted for the optimization or re-optimization of MSP may include one or more of electrode configuration (selection of electrodes for delivering pacing), atrio-ventricular delay(s), interventricular delay(s), intraventricular delay(s), lower rate limit, and pacing threshold(s). The optimization of MSP in general may also include clinical interventions such as medication change. During the optimization or re-optimization of MSP, various pacing configurations (i.e., various combination of pacing parameters to be adjusted) are evaluated. In one embodiment, the one or more pacing parameters to be adjusted for the optimization or re-optimization of MSP are identified based on the potential effect of each parameter in changing the status of heart failure. In one embodiment, when a plurality of pacing parameters are to be adjusted, they are evaluated one at a time, in the order of the potential effect on the status of heart failure, with the pacing parameter identified to have the most significant effect in the status of heart failure being evaluated first. The evaluation of each pacing parameter may include a forward or backward search, i.e., with the value of that pacing parameter starting from the minimum and increase incrementally, or starting from the maximum and decrease incrementally, with the change in the measure of heart failure status recorded for each value evaluated.

FIG. 1 is an illustration of an embodiment of a cardiac rhythm management (CRM) system 100 and portions of an environment in which system 100 operates. CRM system 100 includes an implantable medical device (IMD) 105 that is electrically coup led to a patient's heart through a lead system 108 including implantable leads 110, 115, and 125. An external system 190 communicates with IMD 105 via a telemetry link 185. CRM system 100 is discussed by way of example and not by way of limitation. In various embodiments, the present system can include any types of IMD and lead that can be configured to deliver MSP. For example, while the illustration embodiment allows for MSP pacing using multiple electrodes in the LV, various embodiments allow for MSP pacing using multiple electrodes in either or both of the LV and RV.

IMD 105 includes a hermetically sealed can housing an electronic circuit that senses physiological signals and delivers therapeutic electrical pulses. The hermetically sealed can also functions as an electrode (referred to as "the can electrode" hereinafter) for sensing and/or pulse delivery purposes. IMD 105 senses one or more cardiac signals indicative of cardiac electrical events, including depolarization and repolarization in each of the chambers (RA, RV, LA, and LV), and generates cardiac data representative of the one or more cardiac signals. In one embodiment, IMD 105 includes a pacemaker that delivers cardiac pacing therapies. In another embodiment, IMD 105 includes the pacemaker and a cardioverter/defibrillator that delivers cardioversion/defibrillation therapies. In various embodiments, IMD 105 includes one or more devices selected from monitoring devices and therapeutic devices such as the pacemaker, the cardioverter/defibrillator, a neurostimulator, a drug delivery device, and a biological therapy device.

IMD 105 includes an MSP circuit 130 that is a pacing circuit capable of MSP and can be programmed to deliver various cardiac pacing therapies including MSP or single-site pacing. In various embodiments, MSP circuit 130 can be programmed to provide multi-site or single-site CRT. In various embodiments, MSP circuit 130 senses a heart sound signal and use heart sounds to optimize cardiac pacing therapies including MSP. Various embodiments of MSP circuit 130 are discussed below with reference to FIGS. 2-8.

Lead 110 is an RA pacing lead that includes an elongate lead body having a proximal end 111 and a distal end 113. Proximal end 111 is coupled to a connector for connecting to IMD 105. Distal end 113 is configured for placement in the RA in or near the atrial septum. Lead 110 includes an RA tip electrode 114A, and an RA ring electrode 114B. RA electrodes 114A and 114B are incorporated into the lead body at distal end 113 for placement in or near the atrial septum, and are each electrically coup led to IMD 105 through a conductor extending within the lead body. RA tip electrode 114A, RA ring electrode 114B, and/or the can electrode allow for sensing an RA electrogram indicative of RA depolarizations (P-waves) and delivering RA pacing pulses.

Lead 115 is an RV pacing-defibrillation lead that includes an elongate lead body having a proximal end 117 and a distal end 119. Proximal end 117 is coupled to a connector for connecting to IMD 105. Distal end 119 is configured for placement in the RV. Lead 115 includes a proximal defibrillation electrode 116, a distal defibrillation electrode 118, an RV tip electrode 120A, and an RV ring electrode 120B. Defibrillation electrode 116 is incorporated into the lead body in a location suitable for supraventricular placement in the RA and/or the superior vena cava (SVC). Defibrillation electrode 118 is incorporated into the lead body near distal end 119 for placement in the RV. RV electrodes 120A and 120B are incorporated into the lead body at distal end 119. Electrodes 116, 118, 120A, and 120B are each electrically coupled to IMD 105 through a conductor extending within the lead body. Proximal defibrillation electrode 116, distal defibrillation electrode 118, and/or the can electrode allow for delivery of cardioversion/defibrillation pulses to the heart. RV tip electrode 120A, RV ring electrode 120B, and/or the can of IMD 105 allow for sensing an RV electrogram indicative of RV depolarizations (R-waves) and delivering RV pacing pulses. In various embodiments, proximal defibrillation electrode 116 and/or distal defibrillation electrode 118 may also be used for sensing the RV electrogram. It is noted that while the illustrated embodiment allows for cardioversion/defibrillation, various embodiments allow for MSP using a system with or without cardioversion/defibrillation cap abilities.

Lead 125 is an LV coronary pacing lead that includes an elongate lead body having a proximal end 121 and a distal end 123. Proximal end 121 is coupled to a connector for connecting to IMD 105. Distal end 123 is configured for placement in the coronary vein. Lead 125 includes a plurality of LV electrodes 128A-D. In the illustration embodiment, the distal portion of lead 125 is configured for placement in the coronary vein such that LV electrodes 128A-D are placed in the coronary vein. In another embodiment, the distal portion of lead 125 can be configured for placement in the coronary sinus and coronary vein such that LV electrodes 128A-D are placed in the coronary sinus and coronary vein. In various embodiments, lead 125 can be configured for LV electrodes 128A-D to be placed in various locations in or on the LV for desirable pattern of LV excitation using pacing pulses. LV electrodes 128A-D are each incorporated into the distal portion of lead 125 and are each electrically coupled to IMD 105 through a conductor extending within the lead body. LV electrode 128A, LV electrode 128B, LV electrode 128C, LV electrode 128D, and/or the can electrode allow for sensing an LV electrogram indicative of LV depolarizations (R-Wave) and delivering LV pacing pulses.

Electrodes from different leads may also be used to sense an electrogram or deliver pacing or cardioversion/defibrillation pulses. For example, an electrogram may be sensed using an electrode selected from RV electrode 116, 118, and 120A-B and another electrode selected from LV electrode 128A-D. The lead configuration including RA lead 110, RV lead 115, and LV lead 125 is illustrated in FIG. 1 by way of example and not by way of restriction. Other lead configurations may be used, depending on monitoring and therapeutic requirements. For example, lead 115 may not include defibrillation electrodes 116 and 118 when capability of delivering cardioversion/defibrillation therapy is not needed, additional leads may be used to provide access to additional cardiac regions, and leads 110, 115, and 125 may each include more or fewer electrodes along the lead body at, near, and/or distant from the distal end, depending on specified monitoring and therapeutic needs. In various embodiments, IMD 105 is programmable for sensing the one or more cardiac signals and delivering pacing pulses using any combination of electrodes, such as those illustrated in FIG. 1, to accommodate various pacing configurations as discussed in this document.

External system 190 allows for programming of IMD 105 and receives signals acquired by IMD 105. In one embodiment, external system 190 includes a programmer. In another embodiment, external system 190 includes a patient monitoring system such as the system discussed below with reference to FIG. 3. In one embodiment, telemetry link 185 is an inductive telemetry link. In an alternative embodiment, telemetry link 185 is a far-field radio-frequency telemetry link. Telemetry link 185 provides for data transmission from IMD 105 to external system 190. This may include, for example, transmitting real-time physiological data acquired by IMD 105, extracting physiological data acquired by and stored in IMD 105, extracting therapy history data stored in IMD 105, and extracting data indicating an operational status of IMD 105 (e.g., battery status and lead impedance). The physiological data include the cardiac data representative of the one or more cardiac signals. Telemetry link 185 also provides for data transmission from external system 190 to IMD 105. This may include, for example, programming IMD 105 to acquire physiological data, programming IMD 105 to perform at least one self-diagnostic test (such as for a device operational status), programming IMD 105 to run a signal analysis algorithm (such as an algorithm implementing the tachyarrhythmia detection method discussed in this document), programming IMD 105 to deliver pacing and/or cardioversion/defibrillation therapies, and initiate an MSP optimization procedure in IMD 105 (as further discussed below).

Figure 2:
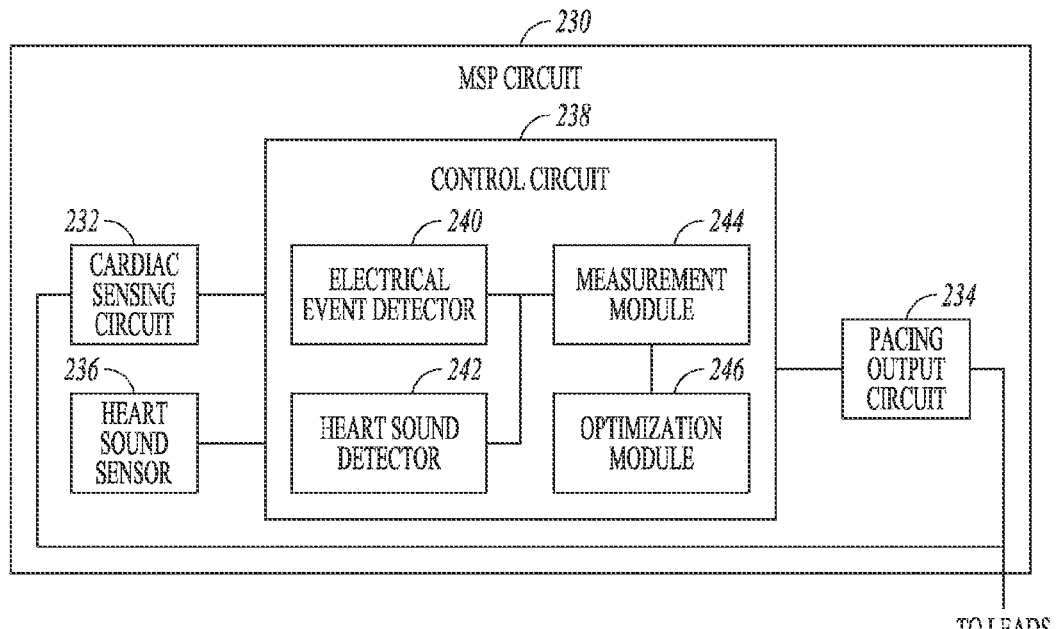
FIG. 2 is a block diagram illustrating an embodiment of a multi-site pacing (MSP) circuit of an implantable medical device (IMD) of the CRM system.

FIG. 2 is a block diagram illustrating an embodiment of am MSP circuit 230, which represents an embodiment of MSP circuit 130. MSP circuit 230 includes a cardiac sensing circuit 232, a pacing output circuit 234, a heart sound sensor 236, and a control circuit 238. Cardiac sensing circuit 232 senses one or more cardiac signals, such as intracardiac electrograms, that are indicative of cardiac electrical events, using leads such as those of lead system 108. Pacing output circuit 234 delivers pacing pulses to the patient's heart though leads such as those of lead system 108. Heart sound sensor 236 senses a heart sound signal indicative of heart sounds. Examples of heart sound sensor 236 include accelerometer and microphone. In the illustrated embodiment, heart sound sensor 236 is housed in the hermetically sealed can of IMD 105. In another embodiment, heart sound sensor 236 can be external to the can, such as incorporated into one of the leads of lead system 108. Control circuit 238 controls the delivery of the pacing pulses using the sensed one or more cardiac signals and a plurality of pacing parameters. In various embodiments, pacing output circuit 234 includes a plurality of pacing output channels each configured to deliver pacing pulses to a pacing site of a plurality of pacing sites in the patient's heart, and control circuit 234 controls delivery of a subset of the pacing pulses from each channel of the plurality of pacing output channels using a subset of the plurality of pacing parameters for that channel.

Control circuit 238 includes an electrical event detector 240, a heart sound detector 242, a measurement module 244, and an optimization module 246. Electrical event detector 230 detects specified-type cardiac electrical events using at least one cardiac signal of the one or more cardiac signals sensed by cardiac sensing circuit 232, with the type specified based on the need for the operation of optimization module 246. Examples of the specified-type cardiac electrical event as needed for optimizing MSP include the Q-waves and the R-waves.

Heart sound detector 242 detects specified-type heart sounds using the heart sound signal sensed by heart sound sensor 236, with the type specified based on the need for the operation of optimization module 246. Examples of the specific-type heart sounds include S1, S2, and S3. An example of a method and circuit for detecting S1, S2, and S3 are discussed in U.S. Pat. No. 7,431,699, entitled, "METHOD AND APPARATUS FOR THIRD HEART SOUND DETECTION," assigned to Cardiac Pacemakers, Inc., which is incorporated herein by reference in its entirety.

Measurement module 244 measures at least one optimization parameter indicative of a status of heart failure (such as a parameter indicative of the patient's hemodynamic response to cardiac pacing) using at least one specified type of heart sounds detected by heart sound detector 242. In various embodiments, measurement module 244 measures one or more optimization parameters each indicative of the status of heart failure (such as one or more parameters indicative of the patient's hemodynamic response to cardiac pacing) using one or more specified types of heart sounds detected by heart sound detector 242 and/or one or more specified types of cardiac electrical events detected by electrical events detector 240. Examples of such optimization parameters include (1) S1 amplitude, such as the measured peak amplitude of the heart sound signal during the detected S or the root-mean-square (RMS) value of the measured peak amplitude, (2) S3 amplitude, such as the measured peak amplitude of the heart sound signal during the detected S3 or the RMS value of the measured peak amplitude, (3) PEP, such as estimated by the measured time interval between the Q or R-wave and the subsequently adjacent S1, (4) ET, such as estimated by the measured time interval between the S1 and the subsequently adjacent S2, and (5) R-S2 interval, which is the measured time interval between the R-wave and the subsequent occurrence of S2. In one embodiment, the diastolic interval, such as estimated by the time interval between the S2 to the subsequently adjacent R-wave, is measured by measurement module 244 for safety check purposes.

Optimization module 246 performs an optimization procedure to optimize MSP by approximately optimizing a pacing configuration in a system capable of delivering MSP. In this document, the "pacing configuration" is defined by one or more parameters approximately optimized by the optimization procedure. In other words, the pacing configuration refers to the setting of the plurality of pacing parameters used for controlling the delivery of the pacing pulses, and an approximately optimized pacing configuration refers to the setting of the plurality of pacing parameters resulting from the optimization procedure. In various embodiments, the optimization procedure approximately optimizes the pacing configuration by approximately optimizing one or more pacing parameters of the plurality of pacing parameters. In various embodiments, the one or more pacing parameters to be approximately optimized are selected based their potential impact on the patient's heart failure status, such as on the patient's hemodynamic performance.

In various embodiments, the optimization procedure approximately optimizes the one or more pacing parameters of the plurality pacing parameters using the at least one optimization parameter measured by measurement module 244. In various embodiments, the pacing pulses are delivered through a plurality of electrodes to the patient's heart. The plurality of electrodes includes a plurality of first ventricular electrodes placed in or on the first ventricle of the patient's heart. The one or more parameters to be approximately optimized include an electrode configuration parameter specifying one or more first ventricular electrodes selected from the plurality of first ventricular electrodes for delivering first ventricular pacing pulses of the pacing pulses to the first ventricle. The first ventricle can be the LV or the RV. In the embodiment illustrated in FIG. 1, the first ventricle is the LV, the first ventricular electrodes includes LV electrodes 128A-D. In various embodiments, the one or more parameters to be approximately optimized also include one or more pacing timing parameters specifying timing of delivery of the first ventricular pacing pulses for each of the specified one or more first ventricular electrodes. Examples of such pacing timing parameters include one or more atrio-ventricular delays, one or more intra-ventricular delays, and one or more inter-ventricular delays. In the embodiment illustrated in FIG. 1, examples of atrio-ventricular delays include pacing time delays each between one of RA electrodes 114A-B and one of LV electrodes 128A-D, examples of intra-ventricular delays includes pacing time delays each between two of LV electrodes 128A-D, and examples of inter-ventricular delays include pacing time delays each between one of RV electrodes 120A-B and one of LV electrodes 128A-D.

In various embodiments, optimization 246 approximately optimizes the pacing configuration (i.e., the one or more pacing parameters) to (1) maximize S1 amplitude, (2) minimize S3 amplitude, (3) minimize paced PEP interval, (4) maximize ET, (5) minimize the ratio of PEP to ET, and/or (6) minimize the R-S2 interval. In various embodiments, a plurality of pacing configurations (different value sets for the one or more pacing parameters) is evaluated during the optimization procedure, and values of the at least one optimization parameter associated with each pacing configuration are measured by measurement module 244 and compared with each other to result in the approximately optimal pacing configuration. In one embodiment, the optimization of the one or more pacing parameters is limited by keeping the diastolic interval within the acceptable range.

Figure 3:
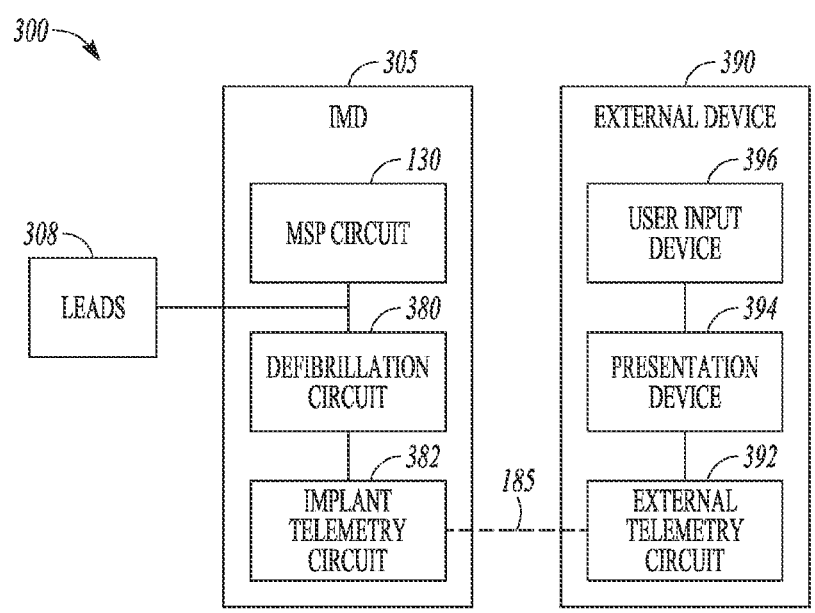
FIG. 3 is a block diagram illustrating an embodiment of the CRM system.

FIG. 3 is a block diagram illustrating an embodiment of a CRM system 300, which represents an embodiment of CRM system 100. CRM system 300 includes leads 308, an IMD 305, and an external device 390. In various embodiments, CRM system 300 allows for delivery of cardiac pacing pulses to a plurality of pacing sites in the patient's heart.

In various embodiments, leads 308 include at least an atrial lead including one or more atrial electrodes and a first ventricular lead including a plurality of first ventricular electrodes. The first ventricular lead allows for delivering MSP. The one or more atrial electrodes are each placed in an atrium. The first ventricular electrodes are to be placed in a first ventricle, with each of the electrodes placed in a first ventricular site of the plurality of pacing sites. In one embodiment, the atrium is the RA and the first ventricle is the LV. In another embodiment, the atrium is the RA and the first ventricle is the RV. In various embodiments, leads 308 includes a second ventricular lead including one or more second ventricular electrodes, in addition to the atrial lead and the first ventricular lead. In one embodiment, the first ventricular lead is an LV lead, and the second ventricular lead is an RV lead. In another embodiment, the first ventricular lead is an RV lead, and the second ventricular lead is an LV lead. Lead system 108 represents a specific example of leads 308, with lead 110 being the atrial lead, lead 125 being the first ventricular lead, and lead 115 being the second ventricular lead.

IMD 305 represents an embodiment of IMD 105 and includes MSP circuit 130, a defibrillation circuit 380, and an implant telemetry circuit 382. Defibrillation circuit 380 delivers cardioversion/defibrillation pulses to the patient heart through leads 308 when such capability is needed. Implant telemetry circuit 382 allows IMD 305 to communicate with external device 390 via telemetry link 185. In one embodiment, implant telemetry circuit 382 receives the optimization command transmitted to IMD 305 for MSP circuit 130 to perform the optimization procedure for optimizing MSP.

External device 390 represents an embodiment of external system 190. In one embodiment, external device 390 includes a programmer for IMDs. External device 390 include a presentation device 394, a user input device 396, and an external telemetry circuit 392. Presentation device 394 presents various types of information to the user, such as information acquired by IMD 305, information indicative of operation of IMD 305 including the current pacing configuration, and information guiding the user to program IMD 305. User input device 396 receives inputs from the user, such as commands controlling the representation of information and commands for programming IMD 305, including the optimization command. External telemetry circuit 382 allows external device 390 to communicate with IMD 305 via telemetry link 185. In one embodiment, upon reception of the optimization command by user input device 396, external telemetry device 392 transmits the optimization commands to IMD 305.

Figure 4:
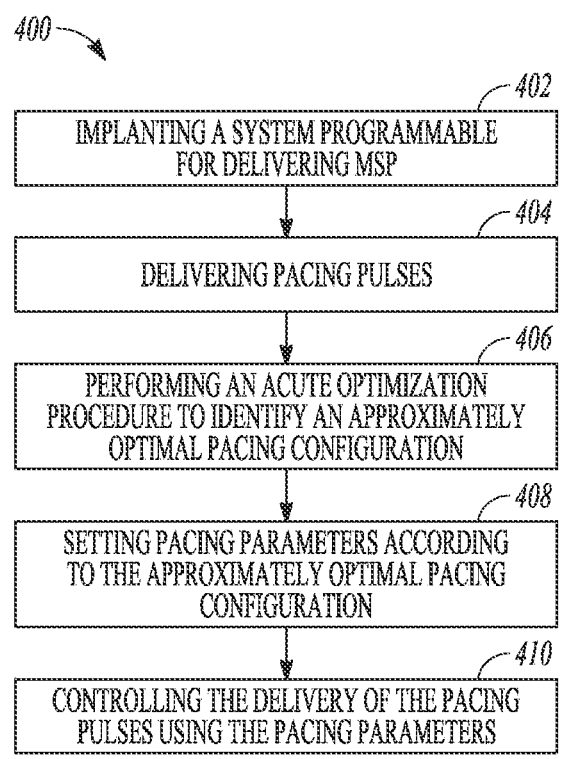
FIG. 4 is a flow chart illustrating an embodiment of a method for delivering cardiac pacing including an acute optimization procedure for approximately optimizing MSP.

FIG. 4 is a flow chart illustrating an embodiment of a method 400 for delivering cardiac pacing including an acute optimization procedure for approximately optimizing MSP. In one embodiment, MSP circuit 130 or 230 is configured to perform method 400.

At 402, an implantable system programmable for delivering MSP is implanted into a patient. Examples of such an implantable system are illustrated as IMD 105 with lead system 108 or IMD 305 with lead system 308. At 404, pacing pulses are delivered to the patient's heart using the implanted system. At 406, an acute optimization procedure is performed to identify an approximately optimal pacing configuration from a plurality of pacing configurations. The pacing configurations are each defined by at least one pacing parameter of a plurality of pacing parameters. In various embodiments, the approximately optimal pacing configuration is identified from a plurality of pacing configurations evaluated during the acute optimization procedure. The plurality of pacing configurations can be predefined and stored in the implantable system and/or dynamically defined based on outcome of the ongoing optimization procedure. In various embodiments, the optimization procedure is performed by executing an optimization protocol, as discussed below with reference to FIG. 5. At 408, the plurality of pacing parameters is set according to the identified approximately optimal pacing configuration. At 410, the delivery of the pacing pulses is controlled using the plurality of pacing parameters.

Figure 5:
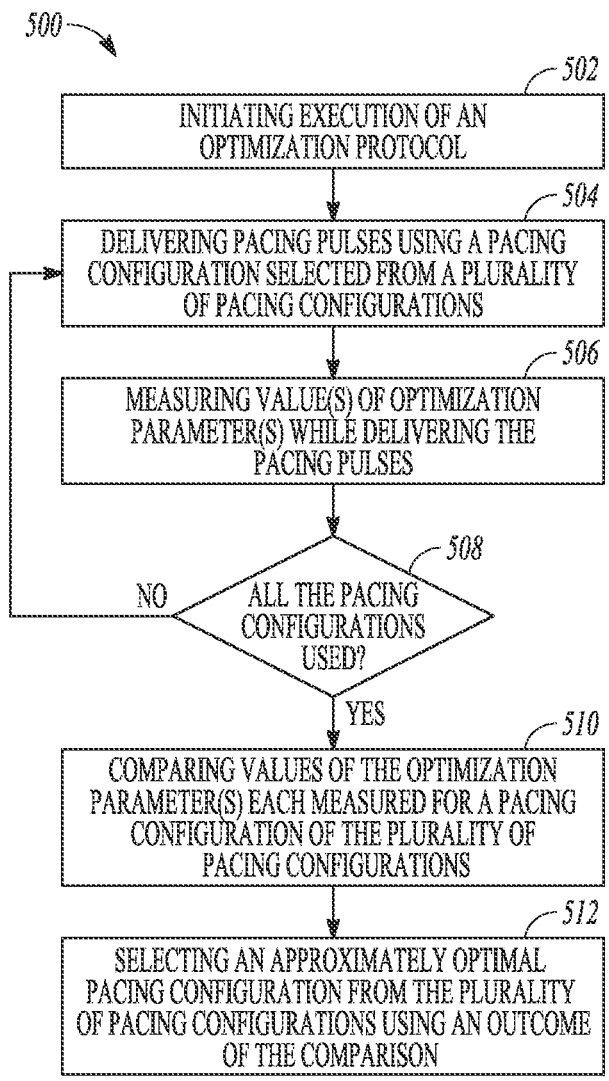
FIG. 5 is a flow chart illustrating an embodiment of a method for executing an MSP optimization protocol.

FIG. 5 is a flow chart illustrating an embodiment of a method 500 for executing an MSP optimization protocol. In one embodiment, method 500 is applied to perform the acute optimization procedure at 406.

At 502, execution of the MSP optimization protocol is initiated in response to an optimization command. In one embodiment, when performing the acute optimization procedure, the optimization command is entered by the user using external system 190 such as external device 390.

At 504, pacing pulses are delivered using a pacing configuration of the plurality of pacing configurations. At 506, a value of at least one optimization parameter is measured while the pacing pulses are delivered using the pacing configuration. Examples of the at least one optimization parameter includes the S1 amplitude, S3 amplitude, PEP, ET, and R-S2 interval, as discussed above. In some embodiments, a plurality of optimization parameters can be measured.

If the values of the at least one optimization parameter has been measured for all the pacing configurations of the plurality of pacing configurations at 508, the measured values are compared to each other at 510. At 512, an approximately optimal pacing configuration is selected from the plurality of pacing configurations using an outcome of the comparison. One example of the comparison and selection is discussed below with reference to FIG. 9.

If the value of the at least one optimization parameter needs to be measured for more pacing configurations of the plurality of pacing configurations at 508, the pacing pulses are delivered using the next pacing configuration from the plurality of pacing configurations at 504, and this continues until the values of the at least one optimization parameter has been measured for all the pacing configurations.

Figure 6:
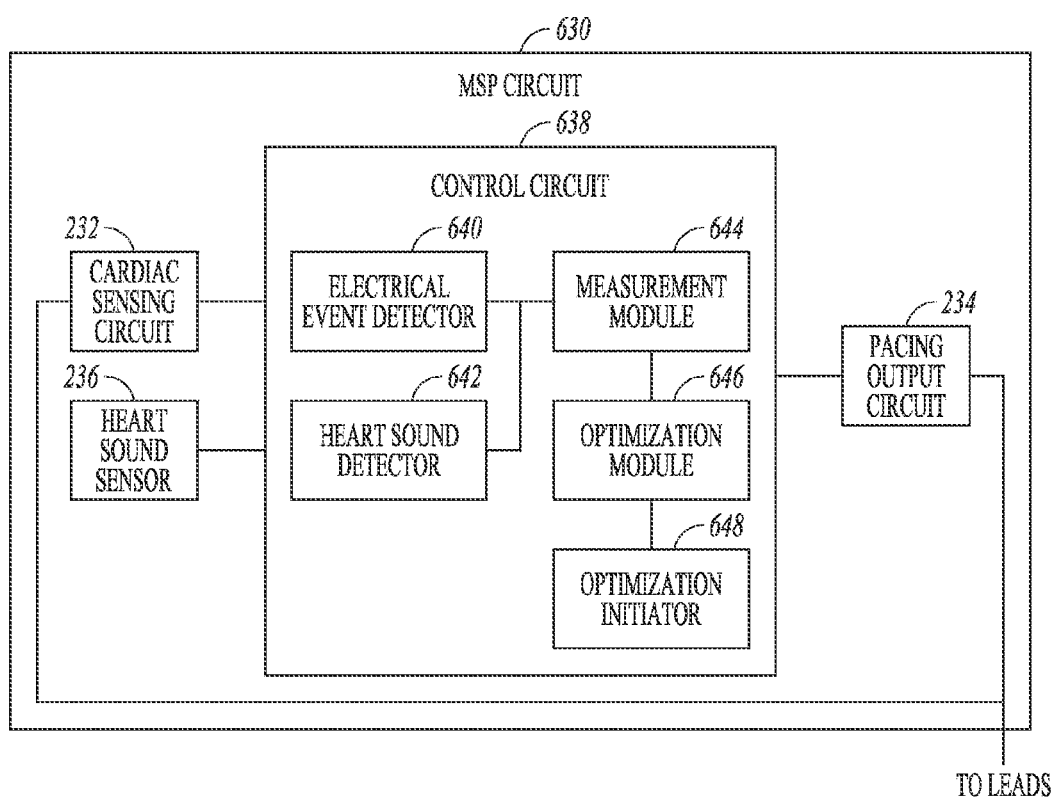
FIG. 6 is a block diagram illustrating another embodiment of the MSP circuit.

FIG. 6 is a block diagram illustrating an embodiment of the MSP circuit 630, which represents another embodiment of MSP circuit 130 and a further embodiment of MSP circuit 230. MSP circuit 630 includes cardiac sensing circuit 232, pacing output circuit 234, heart sound sensor 236, and a control circuit 638. In various embodiments, MSP 630 is configured to perform the functions of MSP 230 and in addition, configured to allow for ambulatory optimization of MSP.

Control circuit 638 includes an electrical event detector 640, a heart sound detector 642, a measurement module 644, an optimization module 646, and an optimization initiator 648. In various embodiments, electrical event detector 640, heart sound detector 642, measurement module 644, and optimization module 646 perform the functions of electrical event detector 240, heart sound detector 242, measurement module 244, and optimization module 246, respectively, and are further configured to accommodate an ambulatory optimization procedure. For example, if the ambulatory optimization procedure requires measurement of an optimization parameter that is different from the at least one optimization parameter measured for the acute optimization procedure, control circuit 638 is configured to measure that different optimization parameter and use it for the ambulatory optimization procedure. In various embodiments, the acute optimization procedure and the ambulatory optimization procedure may specify different pacing parameter(s) to approximately optimize. In other embodiments, the acute optimization procedure and the ambulatory optimization procedure may specify the same pacing parameter(s) to approximately optimize. Examples for the specified-type heart sounds, specified-type cardiac electrical events, optimization parameter, and one or more pacing parameters defining the pacing configuration are as discussed above for control circuit 238. Control circuit 230 and control circuit 638 may use same or different type(s) of heart sounds, same or different type(s) of cardiac electrical events, same or different optimization parameter(s), and same or different pacing configuration(s), such as selected from these examples. In other words, the acute optimization procedure and the ambulatory optimization procedure can use the same optimization protocol (method 500) with the same parameters or different parameters. Control circuit 638 is configured to accommodate both the acute optimization procedure and the ambulatory optimization procedure, and programmable for each of the acute optimization procedure and the ambulatory optimization procedure.

Optimization initiator 648 generates the optimization command, and optimization initiator 648 performs the ambulatory optimization procedure in response to the optimization command. In various embodiments, after an initial optimization of MSP using the acute optimization procedure, re-optimization of the MSP can be performed repeatedly using the ambulatory optimization procedure. In various embodiments, optimization initiator 648 generates the optimization command in response to a user command, based on a predetermined schedule, and/or based on re-optimization criteria. The user command may be entered using external system 190, such discussed above for the acute optimization procedure. The predetermined schedule may specify a time period for the to be performed on a periodic basis. The re-optimization criteria specify one or more types of event that triggers the re-optimization.

In various embodiments, the one or more types of events specified in the re-optimization criteria may each be indicative of a change in the status of heart failure in the patient. The change can be worsening or improvement of the status of heart failure in a way that may suggest a need for re-optimization of MSP. For example, an improvement of the status of heart failure may change the approximately optimal pacing configuration from an MSP pacing configuration to a single-site pacing configuration. Examples of such types of events include (1) a substantial decrease in S1 amplitude (such as by at least 10%), (2) a substantial change in paced S1 waveform morphology from a stored optimal paced S1 waveform template (such as at least 10% change in at least one morphological parameter measured from the paced S1 waveform), (3) a substantial increase in S3 amplitude (such as by at least 5%), (4) a substantial change in a systolic time interval (such as by at least 5%), and (5) a substantial change in a diastolic time interval (such as by at least 5%). In various embodiments, the specified-type events may include any one or more events that can be indicative of a need for the re-optimization of MSP.

Figure 7:
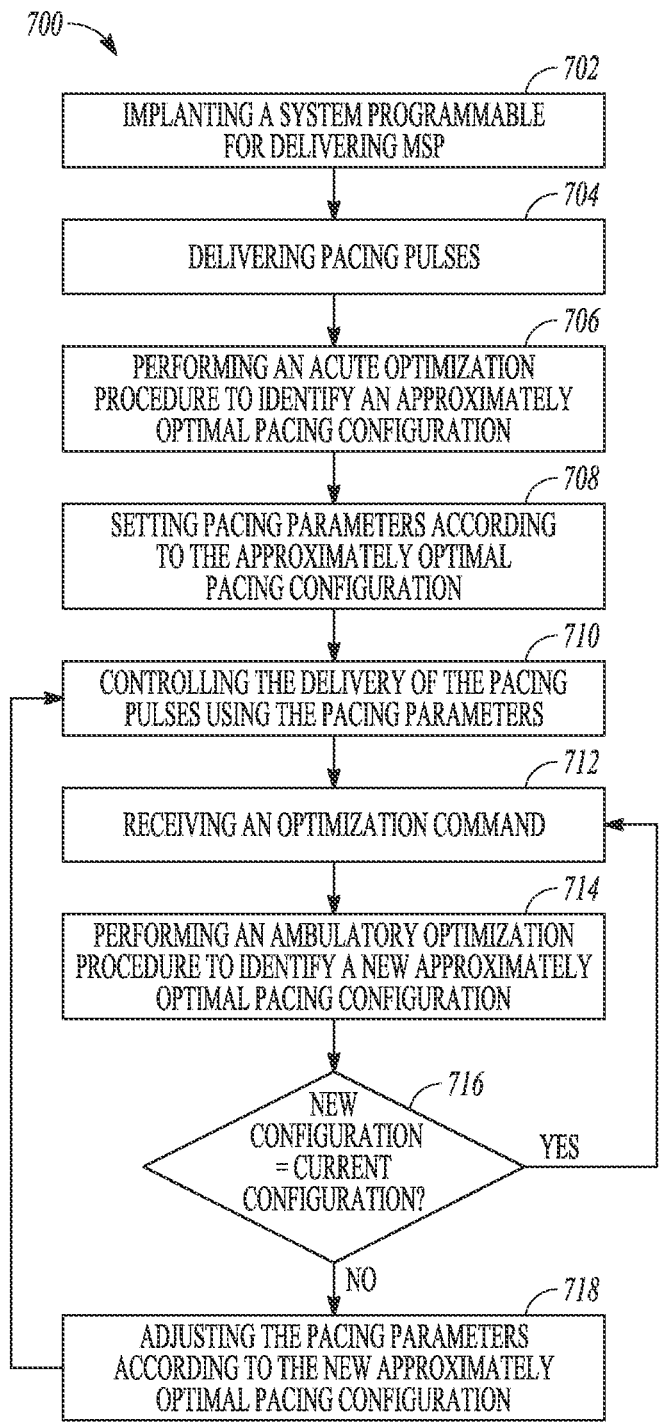
FIG. 7 is a flow chart illustrating an embodiment of a method for delivering cardiac pacing including the acute optimization procedure for approximately optimizing MSP and an ambulatory optimization procedure for approximately re-optimizing the MSP.

FIG. 7 is a flow chart illustrating an embodiment of a method 700 for delivering cardiac pacing including the acute optimization procedure for approximately optimizing MSP and an ambulatory optimization procedure for approximately re-optimizing the MSP. In one embodiment, MSP circuit 130 or 630 is configured to perform method 700.

At 702, an implantable system programmable for delivering MSP is implanted into a patient. Examples of such an implantable system are illustrated as IMD 105 with lead system 108 or IMD 305 with lead system 308. At 704, pacing pulses are delivered to the patient's heart using the implanted system. At 706, an acute optimization procedure is performed to identify an approximately optimal pacing configuration from a plurality of pacing configurations. The pacing configurations are each defined by at least one pacing parameter of a plurality of pacing parameters. In various embodiments, the approximately optimal pacing configuration is identified from a plurality of pacing configurations evaluated during the acute optimization procedure. The plurality of pacing configurations can be predefined and stored in the implantable system and/or dynamically defined based on outcome of the ongoing optimization procedure. In various embodiments, the optimization procedure is performed by executing an optimization protocol, as discussed above with reference to FIG. 5. At 708, the plurality of pacing parameters is set according to the identified approximately optimal pacing configuration. At 710, the delivery of the pacing pulses is controlled using the plurality of pacing parameters.

At 712, an optimization command is received. The optimization command is to initiate a re-optimization of MSP by performing the ambulatory optimization procedure. At 714, the ambulatory optimization procedure is performed to identify a new approximately optimal pacing configuration from the plurality of pacing configurations. In various embodiments, the optimization procedure is performed by executing an optimization protocol, as discussed above with reference to FIG. 5. In various embodiments, same or different type(s) of heart sounds, same or different type(s) of cardiac electrical events, same or different optimization parameter(s), and same or different pacing configuration(s) may be used with the optimization protocol when execution for the acute optimization procedure and the ambulatory optimization procedure, such as discussed above for control circuit 638.

If the new approximately optimal pacing configuration is the same as the current pacing configuration (prior to the ambulatory optimization procedure) at 716, the delivery of the pacing pulses is continued to be controlled using the current pacing configuration. If the new approximately optimal pacing configuration differs from the current pacing configuration at 716, the plurality of pacing parameters is adjusted according to the new approximately optimal pacing configuration at 718. The pacing pulses are continued to be delivered as controlled using the adjusted pacing parameters.

Figure 8:
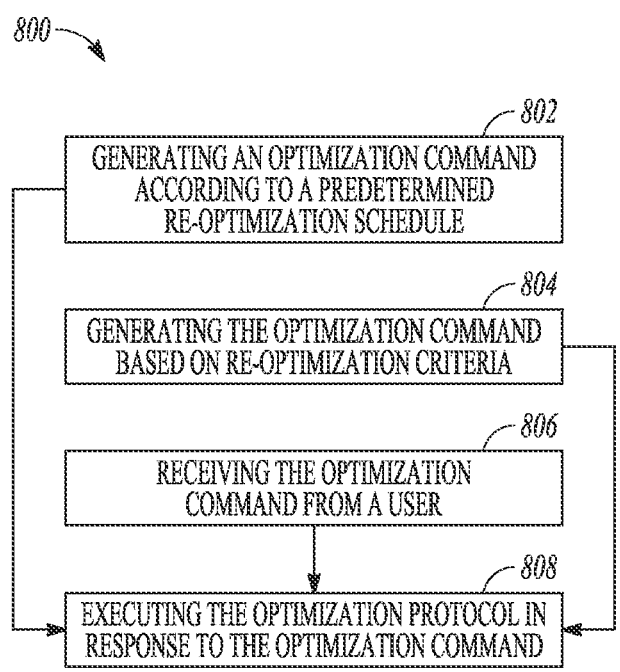
FIG. 8 is a flow chart illustrating an embodiment of a method for initiating the ambulatory optimization procedure.

FIG. 8 is a flow chart illustrating an embodiment of a method 800 for initiating the ambulatory optimization procedure. Method 800 is performed to produce the optimization command to be received at step 712 of method 700. In one embodiment, optimization initiator 648 is configured to perform method 700.

At 802, the optimization command is generated according to a predetermined re-optimization schedule, such as on a periodic basis. At 804, the optimization command is generated based on re-optimization criteria, such as by being triggered by a specified-type event. Examples of the specified-type events include a substantial decrease in S1 amplitude, a substantial change in paced S1 waveform morphology, a substantial increase in S3 amplitude, a substantial change in a systolic time interval, and a substantial change in a diastolic time interval, as discussed above for optimization initiator 648. In various embodiments, the specified-type event may include any one or more events that can be indicative of a need for the re-optimization of MSP, which can be detected from the heart sound signal or any other types of sensed signals. At 806, the optimization command is received from a user. This provides the user with the ability of initiate the ambulatory optimization procedure, for example, in response to an observed event that is not specified in the re-optimization criteria. In various embodiments, any one or more of steps 802, 804, and 806 may be included in method 800. At 808, the optimization protocol is executed in response to the optimization command.

Figure 9:
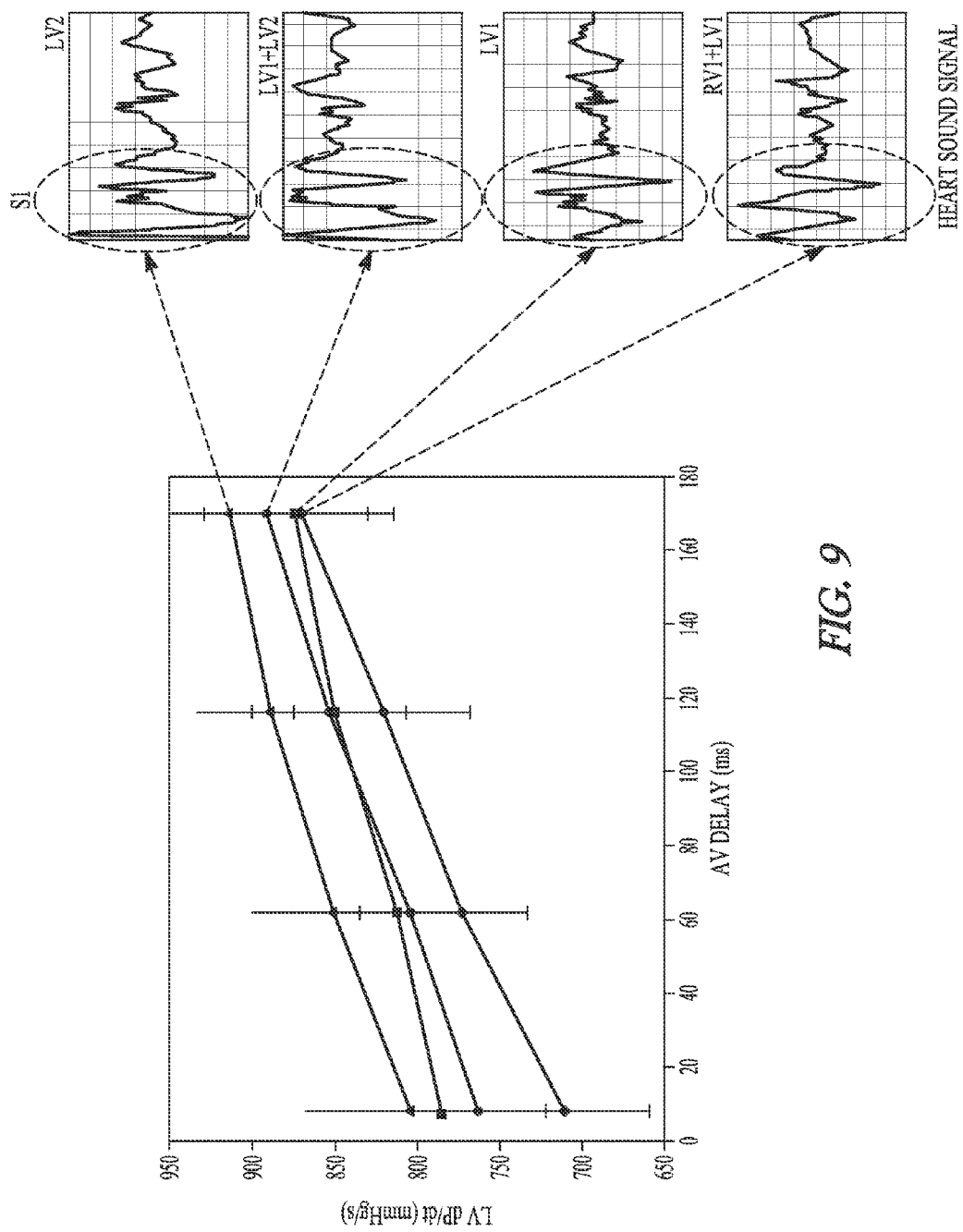
FIG. 9 is an illustration of an example of comparing an MSP configuration to a single-site pacing configuration.

FIG. 9 is an illustration of an example of comparing an MSP configuration to a single-site pacing configuration. The pacing is delivered to treat heart failure, including improving ventricular contractility. The pacing configuration to be approximately optimized is defined by at least an electrode configuration parameter. The system used in the illustrated example includes at least two LV electrodes (LV1 and LV2) and an RV electrode (RV1). The plurality of pacing configurations to be evaluated during the optimization of MSP includes LV2 only (LV single-site), LV1 and LV2 (LV multi-site), LV1 only (LV single-site), and RV1 and LV1 (BiV single-site).

To show the feasibility of optimizing MSP using heart sounds, the rate of change in LV pressure (LV dP/dt) is also determined for each of the pacing configurations at various atrioventricular (AV) delays. The results as seen in FIG. 9 show that the LV single-site pacing with electrode LV1 provides the best performance as indicated by the LV dP/dt (at all AV delays) and by the largest S1 amplitude. This shown that the best single-site pacing may be more efficient than an MSP configuration. An MSP system may provide the best long-term performance as the optimal pacing configuration may change over time as the patient's conditions change. The present method and system as discussed this documents allows the MSP system to operate using an approximate optimal pacing configuration that is up dated to reflect the changes in the patient's condition, among other things.

In various embodiments, the circuit of CRM system 100 may be implemented using a combination of hardware and software. In various embodiments, each element of IMD 105 and external system 190, as illustrated in FIGS. 1-3 and 6, including its various embodiments, may be implemented using an application-specific circuit constructed to perform one or more particular functions or a general-purpose circuit programmed to perform such function(s). For example, control circuit 238 and 638 may be implemented using an application-specific circuit constructed to perform one or more functions discussed as method(s) or method step (s) in this document or a general-purpose circuit programmed to perform such function(s). Such a general-purpose circuit includes, but is not limited to, a microprocessor or a portion thereof, a microcontroller or portions thereof, and a programmable logic circuit or a portion thereof.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for delivering pacing pulses through a plurality of electrodes to a heart having first and second ventricles, the plurality of electrodes including a plurality of first ventricular electrodes placed in or on the first ventricle, the system comprising:
    a cardiac sensing circuit configured to sense one or more cardiac signals;
    a pacing output circuit configured to deliver the pacing pulses;
    a heart sound sensor configured to sense a heart sound signal; and
    a control circuit configured to control the delivery of the pacing pulses using cardiac electrical events and a plurality of pacing parameters, the control circuit including:
    a heart sound detector configured to detect heart sounds including second heart sounds (S2) using the heart sound signal;
    an electrical event detector configured to detect the cardiac electrical events including ventricular depolarization (R-waves) using at least one cardiac signal of the sensed one or more cardiac signals;
    a measurement module configured to measure at least one optimization parameter indicative of hemodynamic response to the delivery of the pacing pulses using the detected heart sounds and to measure an S2-R interval between an occurrence of the S2 and a subsequently adjacent R-wave of the R-waves; and
    an optimization module configured to optimize one or more pacing parameters of the plurality pacing parameters using the measured at least one optimization parameter while keeping the S2-R interval within an acceptable range, the one or more pacing parameters including an electrode configuration parameter specifying one or more first ventricular electrodes selected from the plurality of first ventricular electrodes for delivering first ventricular pacing pulses of the pacing pulses to the first ventricle using the measured at least one optimization parameter and one or more pacing timing parameters specifying timing of the delivery of the first ventricular pacing pulses determined for each electrode of the selected one or more first ventricular electrodes using the measured at least one optimization parameter.

2. The system of claim 1, wherein the heart sound detector is configured to detect first heart sounds (S1) using the heart sound signal, the measurement module is configured to measure an S1 amplitude using the detected S1, and the optimization module is configured to optimize the one or more pacing parameters for maximizing the S1 amplitude.

3. The system of claim 1, wherein the heart sound detector is configured to detect third heart sounds (S3) using the heart sound signal, the measurement module is configured to measure an S3 amplitude using the detected S3, and the optimization module is configured to optimize the one or more pacing parameters for minimizing the S3 amplitude.

4. The system of claim 1, wherein the electrical event detector is configured to detect Q-waves or R-waves using the at least one cardiac signal, the heart sound detector is configured to detect first heart sounds (S1) using the heart sound signal, the measurement module is configured to measure an pre-ejection period (PEP) as a time interval between a Q-wave or R-wave and a subsequently adjacent occurrence of the S1, and the optimization module is configured to optimize the one or more pacing parameters for minimizing the PEP.

5. The system of claim 1, wherein the heart sound detector is configured to detect first heart sounds (S1) and second heart sounds (S2) using the heart sound signal, the measurement module is configured to measure an ejection time (ET) as a time interval between an occurrence of the S1 and a subsequently adjacent occurrence of the S2, and the optimization module is configured to optimize the one or more pacing parameters for maximizing the ET.

6. The system of claim 1, wherein the electrical event detector is configured to detect Q-waves or R-waves using the at least one cardiac signal, the heart sound detector is configured to detect first heart sounds (S1) and second heart sounds (S2) using the heart sound signal, the measurement module is configured to measure an pre-ejection period (PEP) as a time interval between a Q-wave or R-wave and a subsequently adjacent occurrence of the S1 and measure an ejection time (ET) as a time interval between an occurrence of the S1 and a subsequently adjacent occurrence of the S2, and the optimization module is configured to optimize the one or more pacing parameters for minimizing a ratio of the PEP to the ET.

7. The system of claim 1, wherein the electrical event detector is configured to detect R-waves using the at least one cardiac signal, the heart sound detector is configured to detect second heart sounds (S2) using the heart sound signal, the measurement module is configured to measure an R-S2 interval between an R-wave and a subsequently adjacent occurrence of the S2, and the optimization module is configured to optimize the one or more pacing parameters for minimizing the R-S2 interval.

8. The system of claim 1, comprising:
    an implantable medical device including at least the cardiac sensing circuit, the pacing output circuit, and the control circuit; and
    a first implantable ventricular lead configured to be coupled to the implantable medical device and including the plurality of first ventricular electrodes.

9. The system of claim 8, wherein the first implantable ventricular lead is an implantable left ventricular lead.

10. The system of claim 8, wherein the first implantable ventricular lead is an implantable right ventricular lead.

11. The system of claim 8, further comprising:
    an atrial lead configured to be coupled to the implantable medical device and including one or more atrial electrodes; and
    a second ventricular lead configured to be coupled to the implantable medical device and including one or more second ventricular electrodes.

12. A method for pacing a heart having first and second ventricles, the method comprising:
    delivering pacing pulses to the heart through at least a plurality of first ventricular electrodes placed in or on the first ventricle;
    sensing one or more cardiac signals indicative of cardiac electrical events;

sensing a heart sound signal indicative of heart sounds;
measuring at least one optimization parameter indicative of hemodynamic response to the delivery of the pacing pulses using at least the heart sound signal, including measuring an S2-R interval between an occurrence of sound heart sound (S2) and a subsequently adjacent ventricular depolarization (R-wave); and
optimizing one or more pacing parameters of a plurality of pacing parameters using the measured at least one optimization parameter, including:
  optimizing an electrode configuration parameter by identifying one or more first ventricular electrodes from the plurality of first ventricular electrodes for delivering first ventricular pacing pulses of the pacing pulses to the first ventricle using the measured at least one optimization parameter; and
  optimizing one or more pacing timing parameters by determining timing of the delivery of the first ventricular pacing pulses for each electrode of the selected one or more first ventricular electrodes using the measured at least one optimization parameter while keeping the S2-R interval within an acceptable range; and
  controlling the delivery of the pacing pulses using the cardiac electrical events and the plurality of pacing parameters.

13. The method of claim 12, comprising:
measuring a first heart sound (S1) amplitude using the hearing sound signal; and
optimizing the one or more pacing parameters for maximizing the S1 amplitude.

14. The method of claim 12, comprising:
measuring a third heart sound (S3) amplitude using the hearing sound signal; and
optimizing the one or more pacing parameters for minimizing the S3 amplitude.

15. The method of claim 12, comprising:
measuring a pre-ejection period (PEP) using the one or more cardiac signals and the hearing sound signal; and
optimizing the one or more pacing parameters for minimizing the PEP.

16. The method of claim 12, comprising:
measuring an ejection time (ET) using the hearing sound signal; and
optimizing the one or more pacing parameters for maximizing the ET.

17. The method of claim 12, comprising:
measuring a pre-ejection period (PEP) using the one or more cardiac signals and the hearing sound signal;
measuring an ejection time (ET) using the hearing sound signal; and
optimizing the one or more pacing parameters for minimizing a ratio of the PEP to the ET.

18. The method of claim 12, comprising:
measuring an R-S2 interval between a ventricular depolarization (R-wave) and a subsequently adjacent occurrence of sound heart sound (S2) using the one or more cardiac signals and the hearing sound signal; and
optimizing the one or more pacing parameters for minimizing the R-S2 interval.

19. The method of claim 12, wherein delivering the pacing pulses to the heart comprises delivering the pacing pulses to the heart from an implantable medical device through an implantable left ventricular lead coupled to the implantable medical device, the implantable left ventricular lead including the plurality of first ventricular electrodes placed in or on a left ventricle of the heart.

20. The method of claim 12, wherein delivering the pacing pulses to the heart comprises delivering the pacing pulses to the heart from an implantable medical device through an implantable right ventricular lead coupled to the implantable medical device, the implantable left ventricular lead including the plurality of first ventricular electrodes placed in or on a right ventricle of the heart.

* * * * *